United States Patent
Kumar et al.

(10) Patent No.: US 10,561,115 B2
(45) Date of Patent: Feb. 18, 2020

(54) **PROPICONAZOLE RESISTANT MUTANTS OF *CHLORELLA* SPECIES**

(71) Applicant: Reliance Industries Limited, Maharashtra (IN)

(72) Inventors: Chitranshu Kumar, Maharashtra (IN); Niraja Soni, Gujarat (IN); Badrish Ranjitlal Soni, Gujarat (IN); Gautam Das, Andhra Pradesh (IN); Santanu Dasgupta, Mumbai (IN)

(73) Assignee: RELIANCE INDUSTRIES LIMITED, Mumbai, Maharashtra (IN)

( * ) Notice: Subject to any disclaimer, the term of this patent is extended or adjusted under 35 U.S.C. 154(b) by 0 days.

(21) Appl. No.: 15/609,135

(22) Filed: May 31, 2017

(65) Prior Publication Data
US 2017/0349892 A1    Dec. 7, 2017

(30) Foreign Application Priority Data
Jun. 2, 2016 (IN) .............................. 201621019072

(51) Int. Cl.
*A01H 13/00* (2006.01)
*C12R 1/89* (2006.01)

(52) U.S. Cl.
CPC ............... *A01H 13/00* (2013.01); *C12R 1/89* (2013.01)

(58) Field of Classification Search
None
See application file for complete search history.

(56) References Cited

U.S. PATENT DOCUMENTS

2014/0378513 A1* 12/2014 McBride .............. C12Q 1/6895
514/352

OTHER PUBLICATIONS

CCAP results, URL capture for https://www.ccap.ac.uk/results2014.php, retrieved Oct. 9, 2018. (Year: 2018).*
Tuckey et al. (Environmental Toxicology and Chemistry, vol. 21, No. 8, pp. 1715-1723, 2002). (Year: 2002).*
UTEX results, URL capture for https://utex.org/products/utex-0246, retrieved Oct. 9, 2018. (Year: 2018).*
Chinnasanny et al. (Int. J. Mol. Sci. 2009, 10, 518-532). (Year: 2009).*
Deng et al. (African Journal of Agricultural Research vol. 6(16), pp. 3768-3774, Aug. 18, 2011). (Year: 2011).*
Trainor et al. (Journal of phycology 27.3 (1991): 460-461). (Year: 1991).*
Astier et al. (Arch. Microbiol. 120, 93-96 (1979)). (Year: 1979).*

* cited by examiner

*Primary Examiner* — Charles Logsdon
(74) *Attorney, Agent, or Firm* — Westman, Champlin & Koehler, P.A.

(57) ABSTRACT

The present disclosure relates to propiconazole resistant mutants of *Chlorella* sp. having Accession No. CCAP 211/133. The propiconazole resistant mutants of *Chlorella* species have increased tolerance to propiconazole. The present disclosure further provides a method for preparing the propiconazole resistant mutants of *Chlorella* species. The propiconazole resistant mutants of *Chlorella* species can selectively grow in the presence of propiconazole, and hence can be used for large scale production of algal biomass.

3 Claims, 1 Drawing Sheet

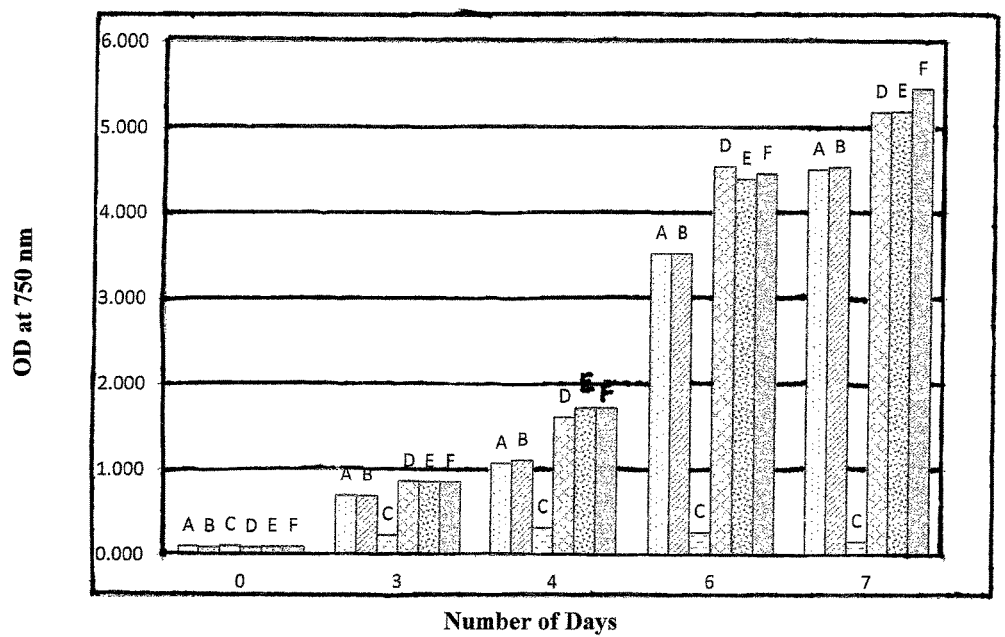

PROPICONAZOLE RESISTANT MUTANTS OF *CHLORELLA* SPECIES

CROSS-REFERENCE TO RELATED APPLICATIONS

This application is a non-provisional application which claims priority to Indian Patent Application No. 201621019072, filed on 2 Jun. 2016, the contents of which are hereby incorporated by reference in its entirety.

FIELD

The present disclosure relates to propiconazole resistant mutants of *Chlorella* species.

DEFINITIONS

As used in the present disclosure, the following terms are generally intended to have the meaning as set forth below, except to the extent that the context in which they are used indicate otherwise.

Grazers: The term "grazers" refer to aquatic pests such as, rotifers, dinoflagellates, ciliates, protozoans and fungi, which decrease the yield of algal biomass/production.

Contaminating organisms: The term "contaminating organisms" refers to filamentous and unicellular cyanobacteria, flagellates, diatoms, etc. which compete with algae in utilization of resources and subsequently result in decrease of algal biomass.

Algae: The term "algae" refers to an informal term for a large, diverse group of eukaryotes that are not necessarily closely related and are thus polyphyletic. Included organisms range from unicellular genera, such as *Chlorella* to multicellular forms, such as the giant kelp, a large brown alga that may grow up to 50 meters in length.

Propiconazole: Propiconazole is a triazole fungicide, also known as a DMI, or demethylation inhibiting fungicide due to its binding with and inhibiting the 14-alpha demethylase enzyme from demethylating a precursor to ergosterol. Without this demethylation step, the ergosterols are not incorporated into the growing fungal cell membranes, and cellular growth is stopped.

BACKGROUND

A major challenge in obtaining large quantities of algal biomass at a very low cost is to attain a continuous and stable production of algae. To achieve this, the algae have to be stably cultivated round the year in open ponds at a sufficiently high density. However, algae when cultivated in open ponds are prone to numerous abiotic and biotic stresses, which lead to frequent culture crashes and productivity losses. Abiotic stress can be taken care to a large extent through bio prospecting, screening and selection of the right kind of algal strains for a particular geographic location and season. Managing contaminants in open ponds along with maintaining high productivity of algae for successful biofuel production is very difficult.

Grazers and contaminating organisms are a major concern in the cultivation of algae. Ciliates, dinoflagellates, rotifers, diatoms, filamentous and unicellular cyanobacteria, flagellates, etc, either feed or compete with the algae for nutrients, resulting in reduced production of the algal biomass. Various chemicals are known, which can be used to kill the grazers and the contaminating organisms, however, these chemicals also have a deleterious effect on the algal growth.

Therefore, there is felt a need for large scale production of algae that mitigates the drawbacks mentioned hereinabove.

OBJECTS

Some of the objects of the present disclosure, which at least one embodiment herein satisfies, are as follows:

It is an object of the present disclosure to ameliorate one or more problems of the prior art or to at least provide a useful alternative.

An object of the present disclosure is to provide propiconazole resistant mutants of *Chlorella* sp.

Another object of the present disclosure is to provide a method for preparing propiconazole resistant mutants of *Chlorella* sp.

Still another object of the present disclosure is to provide propiconazole resistant mutants of *Chlorella* sp. exhibiting enhanced crop protection, increased biomass, using propiconazole resistance selection.

Still another object of the present disclosure is to provide a method for selectively improving the yield of *Chlorella* sp. by controlling grazers and contaminating organisms in an aquatic environment, using propiconazole resistant mutants of *Chlorella* sp.

Other objects and advantages of the present disclosure will be more apparent from the following description, which is not intended to limit the scope of the present disclosure.

SUMMARY

The present disclosure relates to propiconazole resistant mutants of *Chlorella* sp. In one aspect, the propiconazole resistant mutants of *Chlorella* sp. have the characteristics of The Culture Collection of Algae and Protozoa (CCAP) Accession No. CCAP 211/133, having an increased tolerance to propiconazole. The increase in tolerance is defined relative to increase in biomass productivity using the propiconazole resistant mutants of *Chlorella* sp. wherein the increase in biomass productivity is in the range of 10% to 30%.

The propiconazole resistant mutants of *Chlorella* sp. having Accession No. CCAP 211/133 is prepared by subjecting the *Chlorella* sp. cells to UV radiation, reviving the UV treated *Chlorella* culture and treating the revived *Chlorella* culture with a pre-determined concentration of propiconazole, to obtain strains of propiconazole resistant mutants of *Chlorella* sp. resistant to propiconazole. The strains are then separated and each of the strains is separately cultured in a culture media to identify and obtain propiconazole resistant mutants of *Chlorella* sp. strains of exhibiting increase in biomass productivity in the range of 10% to 30%, having Accession No. CCAP 211/133.

In a further aspect of the present disclosure, there is provided a method for selectively controlling the growth of grazers in an aquatic environment. The method includes inoculating the aquatic environment with propiconazole resistant mutants of *Chlorella* sp. having Accession No. CCAP 211/133. The aquatic environment is treated with an effective concentration of propiconazole to selectively control the growth of grazers. Propiconazole can be applied either before inoculating the aquatic environment with the propiconazole resistant mutants of *Chlorella* sp., or after inoculating the aquatic environment with the propiconazole resistant mutants of *Chlorella* sp., or both before and after inoculating the aquatic environment with the propiconazole resistant mutants of *Chlorella* sp.

BRIEF DESCRIPTION OF ACCOMPANYING DRAWING

The disclosure will now be described with reference to the accompanying non-limiting drawing, wherein:

FIG. 1 represents a graph illustrating the growth of wild type *Chlorella sorokiniana* and propiconazole resistant mutants of *Chlorella* sp. having Accession No. CCAP 211/133, in the presence of propiconazole.

DETAILED DESCRIPTION

Algae are a source of various chemicals/compounds having useful commercial applications, such as, generation of renewable energy like bio-fuel which is an alternative to liquid fossil fuels. The use of algae as an alternative for production of bio-oils requires large scale production of the algae. However, controlling the contaminants in open ponds along with maintaining high productivity of algae for successful biofuel production is very difficult. The technologies used to manage such competition or predation in open ponds have proved to be unsuccessful as these methods limit the desired productivity or are incompatible with the algal strain of interest or are unable to act against a wide variety of grazers and contaminating organisms or are economically unviable.

Various chemicals are known, which can be used to kill the grazers and the contaminating organisms, however, these chemicals also have a deleterious effect on the algal growth. Propiconazole is a chemical having a very potent activity against grazers and contaminating organisms. However, propiconazole is algicidal and hence harms the algae as well. The use of chemicals, such as, propiconazole as a crop protection agent in algal cultivation would therefore require algal strains whose growth is not impacted by the presence of propiconazole.

Individual mutants are then isolated and screened to obtain the propiconazole resistant algal mutants of the present disclosure.

Propiconazole is used for screening and selecting algal mutants as it is an effective grazicide at a very low dose. Propiconazole is a potent grazicide at 0.5 ppm and above. It also acts as an endogenous inhibitor of Brassinosteroid (BR) synthesis in plants. BR inhibitors like propiconazole target the inhibition of key enzymes like Cytochrome P450 monooxygenase of BR biosynthetic pathway. It is suggested that the triazole inhibitors like propiconazole inhibit the hydroxylation of the C-22 position of the side chain in BRs by directly binding to DWF4. DWF4, is a cytochrome P450 isolate of putative steroid 22-hydroxylase. The production of Brassinosteroids (BRs) is known and quantified in axenic microalgae strains belonging to Chlorophyceae, Trebouxiophyceae, Ulvophyceae, and Charophyceae family. Two brassinosteroids, viz, brassinolide and castasterone are found in all the algal strains. BR production in *Chlorella* sp. is suggested to enhance cell proliferation, protein and metabolite content.

Accordingly, the present disclosure envisages propiconazole resistant mutants of *Chlorella* sp. that are able to grow in the presence of propiconazole at concentrations that are otherwise toxic to the wild type algae. The ability of the propiconazole resistant mutants of *Chlorella* sp. to grow on propiconazole concentrations that are lethal to the various grazers and contaminating organisms further provide a crop protection benefit for the mutants. These propiconazole resistant mutants of *Chlorella* sp. can yield higher biomass.

The present disclosure also provides a method for preparing propiconazole resistant mutants of *Chlorella* sp. The method includes generating, selecting, isolating and characterizing propiconazole resistant mutants of *Chlorella* sp. Typically, the mutation of the wild type algae can be carried out by UV mutation, gamma mutation, and chemical mutation. In an embodiment of the present disclosure, the mutation of the wild type algae is carried out by UV mutation. After mutation, the algal mutants are subsequently selected and enriched by growing the algal mutants for many generations in the presence of propiconazole.

In accordance with one aspect of the present disclosure, there is provided propiconazole resistant mutants of *Chlorella* sp. having the characteristics of The Culture Collection of Algae and Protozoa (CCAP) Accession No. CCAP 211/133. The propiconazole resistant mutants of *Chlorella* sp. have an increased tolerance to propiconazole.

The increase in tolerance is defined relative to increase in biomass productivity using the propiconazole resistant mutants of *Chlorella* sp. Typically, the increase in biomass productivity is in the range of 10% to 30%.

The present disclosure provides a method for preparing the propiconazole resistant mutants of *Chlorella* sp. having Accession No. CCAP 211/133.

The method comprises subjecting wild type *Chlorella* sp. cells to UV radiation to obtain a UV treated *Chlorella* culture. In an embodiment of the present disclosure, the wild type *Chlorella* sp. is *Chlorella sorokiniana*, and can be sourced from Gagva, Jamnagar, Gujarat, India. Typically, the UV dose can be in the range of 200 mJ/m$^2$ to 700 mJ/m$^2$. Typically, the wild type *Chlorella* sp. is subjected to the aforestated UV dose for a time period in the range of 15 seconds to 120 seconds. The cells are distributed as a monolayer to ensure uniform and efficient penetration of UV. In an embodiment, a UV crosslinker is used for the UV radiation.

The UV treated *Chlorella* culture is then revived to obtain a revived *Chlorella* culture. The cells are typically revived in 12 h light/12 hour dark cycles of white light on culture racks, over a time period in the range of 12 days to 14 days.

The revived *Chlorella* culture is treated with a pre-determined concentration of propiconazole, to obtain strains of propiconazole resistant mutants of *Chlorella* sp., which are resistant to propiconazole. The pre-determined concentration of propiconazole can be in the range of 5 µM to 15 µM. In one embodiment, the concentration of propiconazole is 10 µM. In another embodiment, the revived UV treated propiconazole resistant mutants of *Chlorella* sp. is passed through 30 generations in the presence of 10 µM propiconazole, to enrich the mutant pool.

The strains of propiconazole resistant mutants of *Chlorella* sp. are separated and each strain is separately cultured in a culture media to identify and obtain strains of propiconazole resistant mutants of *Chlorella* sp. that exhibit increase in biomass productivity in the range of 10% to 30%, having Accession No. 211/133.

In one embodiment, the media is urea-phosphoric acid medium.

The present disclosure further provides a method for selectively controlling the growth of grazers in an aquatic environment. The aquatic environment can be fresh water or sea water, and can be selected from the group consisting of outdoor pond, tank for commercial aquaculture, pond for commercial aquaculture, aquarium, and photo-bioreactor. Typically, the pH of the aquatic environment can be in the range of 6.0 to 10.0.

The aquatic environment is inoculated with propiconazole resistant mutants of *Chlorella* species having Accession No. CCAP 211/133. The aquatic environment is treated with an effective concentration of propiconazole, to selectively control the growth of grazers.

In an embodiment, the treatment with is carried out before inoculating the aquatic environment with the propiconazole resistant mutants of *Chlorella* species.

In another embodiment, the treatment with propiconazole is carried out after inoculating the aquatic environment with the propiconazole resistant mutants of *Chlorella* species.

In still another embodiment, the treatment with propiconazole is carried out both before, and after inoculating the aquatic environment with the propiconazole resistant mutants of *Chlorella* species.

Typically, the concentration of propiconazole is in the range of 5 µM to 15 µM.

Adding propiconazole to aquatic environment will kill the grazers, thereby increasing the yield of algae, i.e., propiconazole resistant mutants of *Chlorella* species, and hence selectively improves the yield of the propiconazole resistant mutants of *Chlorella* species in an environment. Propiconazole exhibits very potent activity against grazers and contaminating organisms, and at the same time is a potent algicide. However, the propiconazole resistant mutants of *Chlorella* species of the present disclosure are capable of growing in the presence of propiconazole and their growth is not impacted by the presence of propiconazole.

The propiconazole resistant mutants of *Chlorella* species of the present disclosure can grow in the presence of propiconazole at concentrations that kills the wild type algae. The ability of the propiconazole resistant mutants of *Chlorella* species to grow in the presence of propiconazole provides protection from grazers and contaminating organisms. Further, some of the propiconazole resistant mutants of *Chlorella* species are surprisingly found to have higher biomass.

The present disclosure is further described in light of the following laboratory scale experiments which are set forth for illustration purpose only and not to be construed for limiting the scope of the disclosure. These laboratory scale experiments can be scaled up to industrial/commercial scale and the results obtained can be extrapolated to industrial/commercial scale.

EXPERIMENTAL DETAILS

Experiment-1: Preparation of Propiconazole Resistant Mutants of *Chlorella* Species in Accordance with the Present Disclosure Urea-Phosphoric acid medium having the composition as summarized in Table-1 was used for all the studies.

TABLE 1

| Composition if Urea - Phosphoric acid medium | |
| --- | --- |
| Ingredient | Amount |
| Distilled water | 900 ml |
| Instant ocean salts* | 42 gm/L (gives salinity of 4%) |
| Urea | 3.3 mM |
| Phosphoric acid ($H_3PO_4$) | 0.21 mM |
| Trace elements final concentration below | |
| $FeCl_3$ | 23.4 µM |
| EDTA | 23.4 µM |

TABLE 1-continued

| Composition if Urea - Phosphoric acid medium | |
| --- | --- |
| Ingredient | Amount |
| $CuSO_4\ 5H_2O$ | 78.6 nM |
| $Na_2MoO_4\ 2H_2O$ | 52 nM |
| $ZnSO_4\ 7H_2O$ | 0.153 µM |
| $CoCl_2\ 6H_2O$ | 84 nM |
| $MnCl_2\ 4H_2O$ | 1.82 µM |
| Adjust pH to 7.5 and make volume to 1 L using distilled water | |

*Instant Ocean was procured from Aquarium systems Inc. USA.

Step-I: UV Mutation Procedure $1 \times 10^7$ Cells/mL wild type *Chlorella sorokiniana* cells (Gagva, Jamnagar, Gujarat, India) at log phase of growth ($O.D_{750}$ 0.5-0.7) were taken and centrifuged at 5000 rpm for 10 minutes at 30° C. to obtain a pellet. The pellet was re-suspended in 10 ml of Urea-Phosphoric acid medium and placed on a glass petri plate (autoclaved) without lid. Care was taken to ensure that the cells formed a monolayer on the glass plate, so as to aid in efficient and uniform UV penetration. The cells were exposed to UV radiation in UV crosslinker for different times (30 seconds to 90 seconds) depending on the UV dose (300-500 mJ/m$^2$). After completion of the UV exposure, the cells were collected into a 50 ml tube and kept in dark for 24 hours. After 24 hours, the cells were centrifuged at 5000 rpm for 10 minutes at room temperature and re-suspended in 5 ml of Urea-Phosphoric acid medium in culture tube.

Cell viability of Untreated (control) and UV exposed cells was calculated using nucleic acid dye (Sytox green). 0.5 µM of the dye was used for staining and incubated for 5 minutes in the dark. The cells were analyzed on flow cytometer. Killing was about 40-60% using UV radiation. Cells were revived in 12 h light/12 hour dark cycles of white light on culture racks. The revival of the cells took 12-14 days.

Step-II: Enrichment of Propiconazole Resistant Mutants of *Chlorella* Species

UV mutagenized and revived cells were exposed to sub lethal concentration of propiconazole (10 µM). To enrich the mutant pool, the UV mutagenized culture was passed through 30 generations in the presence of 10 µM propiconazole.

Step-III: Separation, Isolation and Identification of Individual Propiconazole Resistant Mutants of *Chlorella* Strains The enriched mutant pool was plated on 0.8% agar plates containing 10 µM propiconazole. About 350 isolated colonies were obtained. These individual propiconazole resistant mutants of *Chlorella* species resistant to propiconazole were patched on 0.8% agar plates containing 10 µM propiconazole. These mutants were then inoculated in 2 mL of sterile liquid Urea-Phosphoric acid medium in culture tubes. This was scaled up to 10 mL of sterile liquid Urea-Phosphoric acid medium in 50 mL flasks. The growth kinetics of individual mutants was carried out with and without 10 µM propiconazole in 250 mL flask using 70 mL medium.

Strains of propiconazole resistant mutants of *Chlorella* species exhibiting increase in biomass productivity in the range of 10% to 30% were identified and deposited at the Culture Collection of Algae and Protozoa (CCAP), SAMS Limited, Scottish Marine Institute, OBAN, Argyll PA37 1QA, Scotland, United Kingdom, having the Accession No. CCAP 211/133 (*Chlorella sorokiniana* PcZ-1).

Experiment-2: Study of Wild Type *Chlorella sorokiniana* and Propiconazole Resistant Mutants of *Chlorella* Species in the Presence of Propiconazole

*Chlorella sorokiniana* cells (Wild type) and propiconazole resistant mutants of *Chlorella* species (PcZ-1) were inoculated at 0.1-0.15 OD@750 nm (each set in triplicates). To verify the effect of methanol (propiconazole was dissolved in methanol), one set was treated with 0.1% methanol. One set of flasks in triplicate of Wild type and PcZ-1 mutants were inoculated with and without 10 μM propiconazole. After inoculation flasks were kept in 12 h light/12 hour dark cycles of white light in an incubator shaker at 100 rpm. The temperature was 28° C., 70% humidity and 2% ambient $CO_2$. 3 mL sample was removed each day, to determine the Optical density (OD) of the culture at 750 nm. The results obtained are as illustrated in FIG. 1.

FIG. 1 illustrates a graph of the growth comparison between wild type *Chlorella sorokiniana* and propiconazole resistant mutants of *Chlorella* species *Chlorella sorokiniana* mutant PcZ-1, in the presence of propiconazole, wherein A represents wild type *Chlorella sorokiniana* grown in the absence of propiconazole, B represents wild type *Chlorella sorokiniana* grown in the presence of 0.1% methanol, C represents wild type *Chlorella sorokiniana* grown in the presence of 10 μM propiconazole, D represents PcZ-1 grown in the absence of propiconazole, E represents PcZ-1 grown in the presence of 0.1% methanol, and F represents PcZ-1 grown in the presence of 10 μM propiconazole. Growth of the wild type *Chlorella sorokiniana* is inhibited in the presence of propiconazole and typically the culture crashes after a few days. The propiconazole resistant mutants of *Chlorella* species (PcZ-1) was not affected by the presence of propiconazole, and continued to grow. Further, some of them resulted in 10% to 30% higher biomass in the absence of propiconazole as compared to the wild type progenitor strain. The percent increase in growth of PcZ-1 calculated from FIG. 1, is summarized in Table-2.

TABLE 2

Comparison of Wild type *Chlorella sorokiniana* without propiconazole and PcZ-1 with and without 10 μM propiconazole

| No. of days | % increase PcZ-1 | | | PcZ-1 + 10 μM PcZ | | | Average % increase PcZ-1 | PcZ-1 + 10 uM PcZ |
|---|---|---|---|---|---|---|---|---|
| 4 | 54.5 | 48.1 | 47.6 | 45.5 | 66.7 | 68.6 | 50.1 | 60.2 |
| 6 | 16.3 | 46.0 | 26.8 | 17.3 | 38.7 | 25.4 | 29.7 | 27.1 |
| 7 | 7.4 | 20.0 | 17.6 | 10.6 | 29.4 | 23.2 | 15.0 | 21.1 |

It is clearly seen from FIG. 1 and Table-2 that the propiconazole resistant mutants of *Chlorella* species of the present disclosure show higher biomass productivity as compared to that of the wild type in the present of propiconazole. The higher biomass of the propiconazole resistant mutants of *Chlorella* sp. CCAP 211/133 may be due to the enhanced Brassinosteroid (BR) production by the mutant strains. BR's are steroidal plant hormones that play important roles in plants in regulating cell growth, division as described above.

TECHNICAL ADVANCEMENTS

The present disclosure described herein above has several technical advantages including, but not limited to, the realization of:
propiconazole resistant mutants of *Chlorella* sp.;
a method for preparing propiconazole resistant mutants of *Chlorella* sp.;
a method for preparing mutants having increased biomass capability using propiconazole selection;
outdoor cultivation of algae without culture crashes due to contamination by grazers and contaminating organisms; and
large scale production of algae devoid of any contamination from grazers and contaminating organisms.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

We claim:

1. A propiconazole resistant mutant strain of *Chlorella sorokiniana* having the Culture Collection of Algae and Protozoa (CCAP) Accession number CCAP 211/133.

2. A method for selectively controlling the growth of grazers in an aquatic environment; said method comprising the following steps:
   a. inoculating said aquatic environment with the propiconazole resistant mutant strain of *Chlorella sorokiniana* having Accession No. CCAP 211/133 of claim 1; and b. treating said aquatic environment either before or after step a) or both before and after step a) with an effective concentration of propiconazole to selectively control the growth of grazers.

3. The method as claimed in claim 2, wherein the concentration of said propiconazole is in the range of 5 μM to 15 μM.

* * * * *